United States Patent [19]

Hill

[11] Plant 4,802

[45] Jan. 19, 1982

[54] BURN-RESISTANT JAPANESE YEW

[75] Inventor: Platt W. Hill, West Dundee, Ill.

[73] Assignee: D. Hill Nursery, Union, Ill.

[21] Appl. No.: 98,076

[22] Filed: Nov. 28, 1979

[51] Int. Cl.[3] ..... A01H 7/00
[52] U.S. Cl. ..... Plt./50
[58] Field of Search ..... Plt./50

[56] References Cited

U.S. PATENT DOCUMENTS

P.P. 2,052 4/1961 Wyman ..... Plt./50

OTHER PUBLICATIONS

Shrubs & Vines for American Gardens, Wyman, 3rd Ed., 1973, MacMillan Publ. Co., N.Y., (pp. 458–461).

*Primary Examiner*—Robert E. Bagwill
*Attorney, Agent, or Firm*—Cook, Wetzel & Egan, Ltd.

[57] ABSTRACT

A Japanese Yew plant has been discovered and asexually reproduced which is resistant to "winter burn" from severe winter weather in cold extremes of temperate zone climates. The plant has flat needles, shiny green on top and paler green below, the terminal ends having single sharp points. The bark of the stems is reddish brown and glossy. The buds are ovoid oblong, green in the spring and summer, and change to brown in the fall. The foliage is dense and tends to spread.

2 Drawing Figures

Evergreen plants for domestic residential and institutional landscapes are widely used. However, in the cold extremes of temperate climates, such as the Northern U.S., evergreens are sometimes subject to winter burn from severe winter weather. Hard freezing and thawing appears not only to kill and turn parts of the foliage brown, but to stunt plants' growth through the killing of buds. The new plant disclosed herein is most closely related to the known variety, "*taxus cuspidata thayerae*", which is extremely susceptible to winter burn damage.

A new variety of Japanese Yew, "*Taxus cuspidata* Spring Green", has been discovered which is noted for its resistance to stunting and browning of foliage from winter burn even in the cold extremes of temperature climates. Mature leaves are of a flat needle type, 1.5 to 1.8 cm long, each of which comes to a sharp point. Each leaf is shiny green on top and a paler green on the underside. Stems are reddish-brown and glossy. A twelve year old plant from a rooted cutting has typically grown eighteen to twenty-four inches high and four to five feet across, being denser and more compact than the "*taxus cuspidata thayerae*" variety.

In the photographs,

Figure 1:
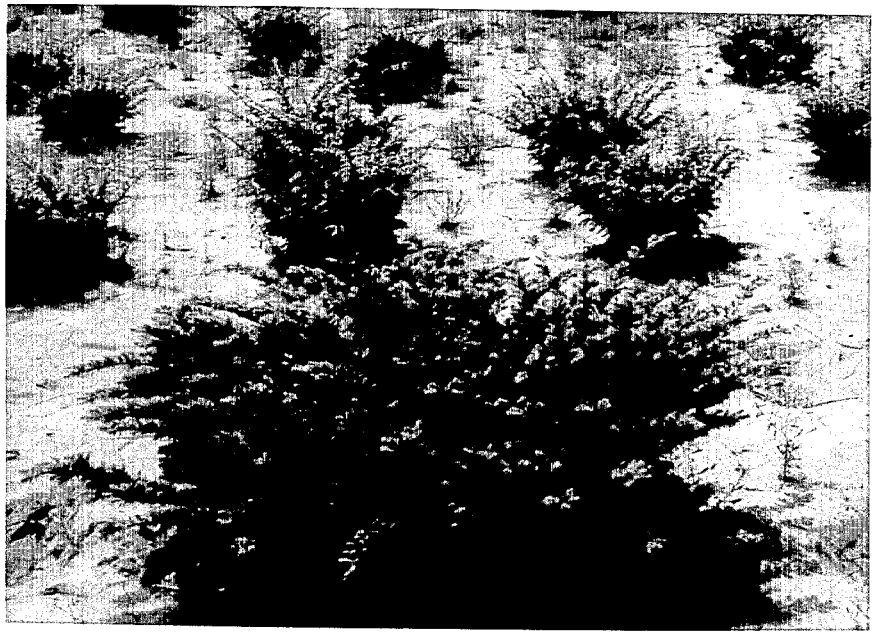
FIG. 1 is an overall view of the *Taxus cuspidata* Spring Green plant in the foreground with conventional "*taxus cuspidata thayerae*" plants in the background.
Figure 2:
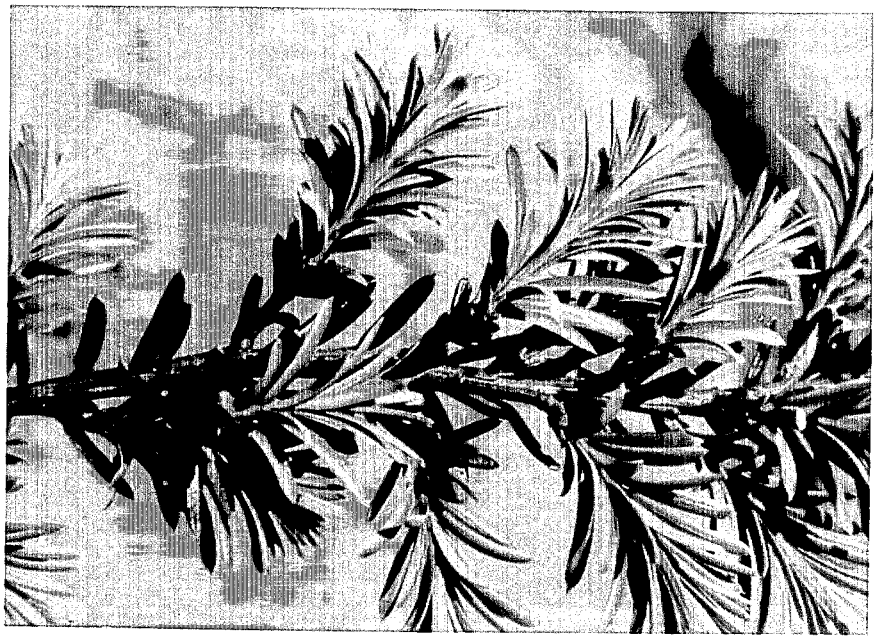
FIG. 2 is a close-up detail of mature foliage of a *Taxus cuspidata* Spring Green plant.

All the known plants of the present, new variety can be traced to one of a group of eighteen plants including some "*taxus cuspidata thayerae*" variety brought from now unknown sources to an experimental area at Dundee, Ill., prior to 1955. All of these plants were experimentally reproduced in 1967 by the rooting of cuttings from the original plants. The rooted cuttings were later planted in fields at Union, Ill., for further testing. In the spring of 1977, after an unusually severe winter, the winter burn resistance of all of the cuttings from one of the original eighteen plants was recognized as superior for the first time. Additional rooted cuttings from these burn-resistant plants have all exhibited the same burn-resistant features in field tests after the equally-severe winters of 1978 and 1979. These plants have grown much larger more quickly than their nearest relatives in the same soil, as seen in FIG. 1. The experimental area at Union, Ill., is an open field of sandy clay loam, entirely flat with widely spaced rows of evergreen shrubs.

The foliage of *Taxus cuspidata* Spring Green comprises leaves of a flat needle type 1.5 to 1.8 cm long, each coming to a sharp point at its end. Each leaf is shiny green in color on top and has a paler green color on the underside. Each leaf has a slightly leathery texture. The leaves are formed radially on the stem and point mostly upward. The bark of the stems is reddish-brown and glossy in mature portions. Buds of *Taxus cuspidata* Spring Green are ovoid oblong in shape. They are green in the spring and summer, and change to brown in the fall.

While no plant of the new variety appears to have reached maturity, a twelve year old specimen grown from a rooted cutting has typically reached a size of one and a half to two feet (45 to 60 cm) in height and four to five feet (120 to 150 cm) across. The foliage tends to spread about the stem of the initial plant. *Taxus cuspidata* Spring Green is denser and more compact than the related "*taxus cuspidata thayerae*" variety. The new variety has not shown any winter burn symtoms at Union, Ill., where winter temperatures have reached as low as 23 degrees below zero Fahrenheit (minus 31 degrees Celsius) and has grown much larger in size than similar "*taxus cuspidata thayerae*" cuttings. *Taxus cuspidata* Spring Green distinguishes from the variety of *Taxus cuspidata* plant awarded U.S. Plant Pat. No. 2,052, to Richard Wyman, Jr., referred to as "Green Wave". First, Spring Green has smaller needles, on average, than the Green Wave plant, with ranges of 1.5 to 1.8 cm. versus 1.5 to 2.5 cm., respectively, being observed. The colors of the leaf petioles are distinctly different, those of the Spring Green plant being a much darker, reddish-brown, while those of the Green Wave are a light brown. The stem colors of the Green Wave and Spring Green plants are distinctly different, the terminal branches of the Spring Green plant being the same reddish-brown as that of its petioles, while the Green Wave plant stems are a light green on the terminal branches. The Wyman Green Wave plant has been propagated only in the east, where winters are humid and no commercially significant winter burn problem has been experienced.

Asexual reproduction has been carried out by and under the direction of the inventor by conventional rooting of cuttings from the parent plant. Cuttings were taken and rooted indoors, followed by transplanting to outdoor soil in the experimental area of the commercial nursery at Union, Ill.

I claim as my invention:

1. The new and distinct variety of "*Taxus cuspidata* Spring Green" plant as described and illustrated in the foregoing specification characterized particularly by hardy resistance to stunting of growth and browning of foliage caused by winter burn.

* * * * *